Figure 1:
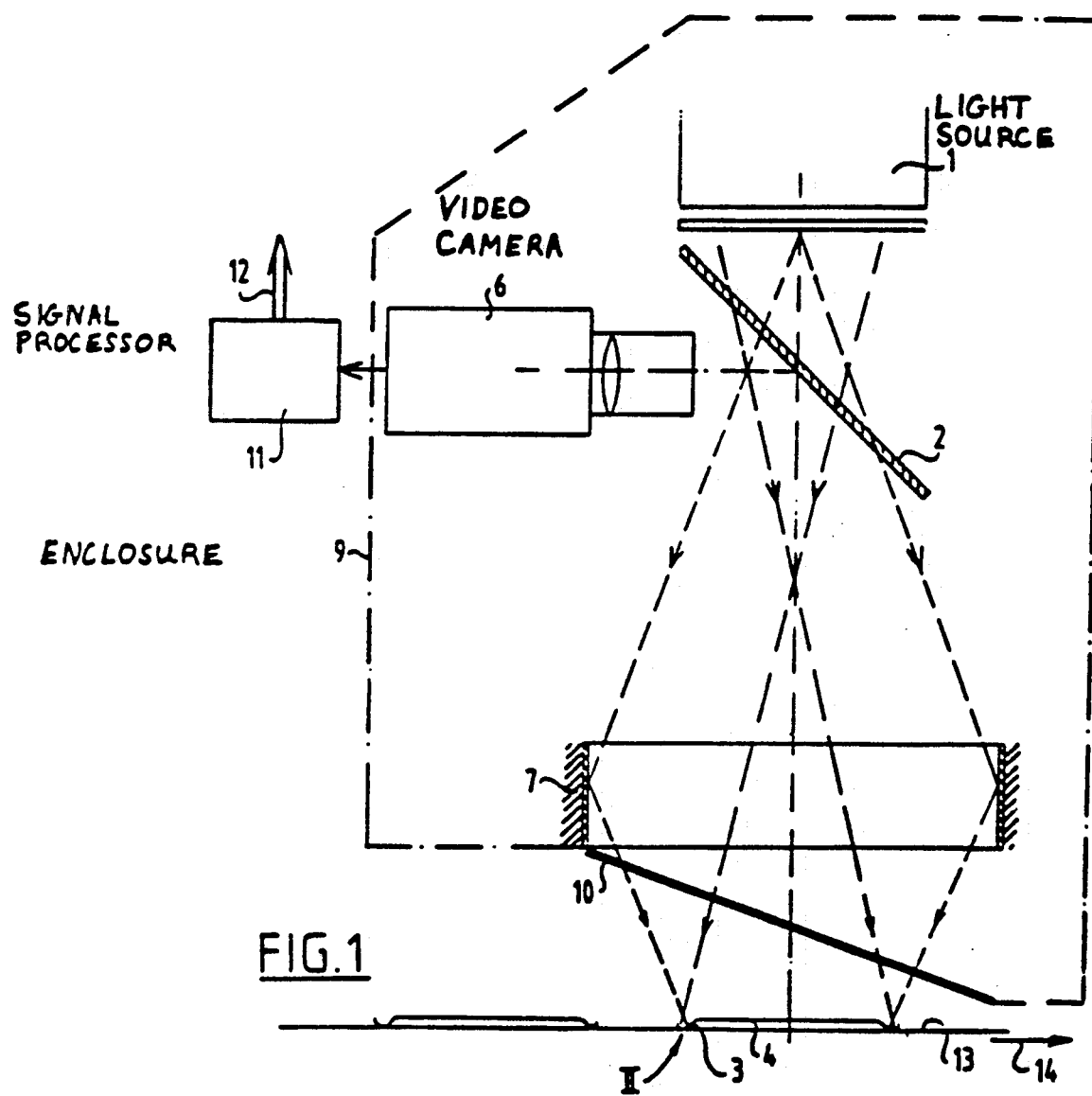

United States Patent [19]

Swart

[11] Patent Number: 5,011,289

[45] Date of Patent: Apr. 30, 1991

[54] METHOD AND AN APPARATUS FOR CHECKING AN OBJECT FOR THE PRESENCE OF FILLING COMPOUND

[75] Inventor: Nicholaas C. Swart, Deventer, Netherlands

[73] Assignee: Heuft-Qualiplus B.V., Deventer, Netherlands

[21] Appl. No.: 439,543

[22] Filed: Nov. 20, 1989

[30] Foreign Application Priority Data

Nov. 21, 1988 [NL] Netherlands ................. 8802870

[51] Int. Cl.$^5$ ............................................. G01N 21/88
[52] U.S. Cl. ................................... 356/394; 356/237; 358/101; 358/106
[58] Field of Search ................ 356/394, 237; 358/101, 358/106; 382/8

[56] References Cited

U.S. PATENT DOCUMENTS

| | | | |
|---|---|---|---|
| 4,037,724 | 7/1977 | Schultz et al. | 209/111.7 |
| 4,873,432 | 10/1989 | Alderman | 356/237 |

FOREIGN PATENT DOCUMENTS

| | | |
|---|---|---|
| 52-43484 | 5/1977 | Japan . |
| 59-92333 | 5/1984 | Japan . |
| 60-201241 | 10/1985 | Japan . |
| 2204125 | 11/1988 | United Kingdom . |

Primary Examiner—F. L. Evans
Attorney, Agent, or Firm—Willian, Brinks, Olds, Hofer, Gilson & Lione

[57] ABSTRACT

The invention relates to a method for inspecting the filling with sealing compound of a gutter present in an object, e.g. a metal lid. Such a method can according to the invention take place by carrying out the following steps:

(1) providing an object to be inspected;
(2) directing a light beam on said gutter;
(3) previously determining the shape of the reflection picture of at least said gutter of an object satisfying a predetermined standard;
(4) determining the picture of said gutter;
(5) comparing the results of steps (4) and generating a rejection signal in case of a detected deviation outside a chosen tolerance range. Should only e.g. a diverging beam be used, it can happen that a local lack of filling compound is not detected by a sensing device, since from the zone in question no reflection in the direction of the sensing device can take place as a result of shadow-effect. In view thereof according to the invention preference is given to a method which is characterized by
(6) carrying out step (2) in such a way that the gutter is illuminated from two directions which are both substantially perpendicular on the axis of said gutter and forming an angle with the plain of the gutter between about 45° and 90°, and 135° and 90°, respectively. Here use is made of two beams, one divergent and one convergent, respectively.

9 Claims, 2 Drawing Sheets

FIG.1

METHOD AND AN APPARATUS FOR CHECKING AN OBJECT FOR THE PRESENCE OF FILLING COMPOUND

The invention relates to a method for inspecting the filling with sealing compound of a gutter present in an object, e.g. a metal lid.

Such a method can according to the invention take place by carrying out the following steps:

(1) providing an object to be inspected;.
(2) directing a light beam on said gutter;
(3) previously determining the shape of the reflection picture of at least said gutter of an object satisfying a predetermined standard;
(4) determining the picture of said gutter;
(5) comparing the results of steps (4) and generating a rejection signal in case of a detected deviation outside a chosen tolerance range.

Should only e.g. a diverging beam be used, it can happen that a local lack of filling compound is not detected by a sensing device, since from the zone in question no reflection in the direction of the sensing device can take place as a result of shadow-effect. In view thereof according to the invention preference is given to a method which is characterized by (6) carrying out step (2) in such a way that the gutter is illuminated from two directions which are both substantially perpendicular on the axis of said gutter and forming an angle with the plain of the gutter between about 45° and 90°, and 135° and 90°, respectively. Here use is made of two beams, one divergent and one convergent, respectively.

In the last-mentioned case e.g. use may be made of an apparatus having a light source directly illuminating with a diverging beam the gutter of an object to be inspected, and with a converging beam by means of reflection via a substantially cylindrical mirror which is coaxially positioned relative to the object.

Figure 2:
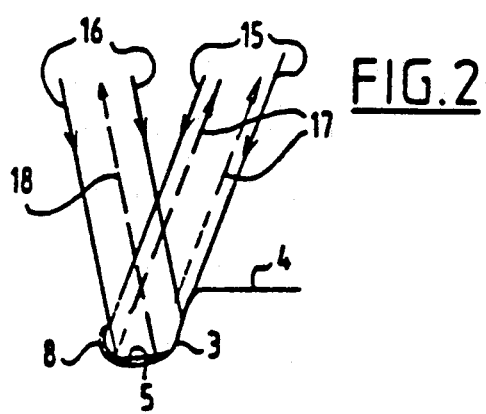

The invention will now be explained with reference to the accompanying drawings. In the drawings:

FIG. 1 is a schematic sectional view of an apparatus according to the invention; and FIG. 2 is the detail II of FIG. 1.

FIG. 1 shows a lamp 1, in this case a stroboscope-lamp, which via a half-transparent mirror 2 illuminates the gutter 3 of a lid 4, in which filling compound 5 has been applied (see FIG. 2). On places where this filling mass or compound 5 is absent, the reflection of the light by the bottom of the gutter will be substantially stronger than in case of filling compound 5 being present.

A video-camera 6 senses the gutter 5 by means of reflection through the half-transparent mirror 2. If gutter 3 is in accordance with the standard filled with filling compound 5, the video-camera 6 senses a dark annular gutter. Regions with lacking filling compound can be sensed as bright spots in this ring, which can readily be detected by means of existing techniques for processing pictures.

The reflection direction of the light is dependent on the angular position of the reflecting surface. Since the reflection of light directly emanating from lamp 1 from the inner side of gutter 3 is directed in a direction outside the angle of view of the camera, there no lacking filling compound will be detected.

By illuminating said surface from an other direction by means of a cylindrical mirror 7 the mentioned area, in this case of lacking of filling compound 5, will also reflect light in the direction of camera 6.

Also other defects of gutter 3 affecting the picture of the edge zone sensed by camera 6 can in this arrangement be detected. This is e.g. the case with too low an upstanding edge 8 of gutter 3.

In order to safeguard the optical apparatus against external influences, such as dust, water, etc. the optical parts 1, 2, 6, 7 are enclosed by a closed housing 9. Through a glass plate 10 the lid 4 is illuminated and sensed. This glass plate 10 is arranged under an angle in order to avoid that light reflected by glass plate 10 reaches the video-camera 6.

A signal processing unit 11 receives the video signals from video-camera 6, which signals correspond with the picture of the gutter 3. This signal processing unit 11 comprises a memory, in which previously the shape of the reflection picture of the gutter in case of a lid satisfying a predetermined standard is stored. Also the signal processing unit 11 comprises comparing means for comparing the output signal of the video-camera and the contents of said memory. These comparing means generate a rejection signal in case of a detected deviation outside a chosen tolerance range. The rejection signal can be supplied through an output 12 to eject-means (not-shown) adapted to eject the lid in question from a continuous flow of lids, which are successively inspected by the apparatus according to the invention.

In such an apparatus the lids are successively transported on conveyor 13 in the direction of arrow 14 below the glass plate 10 serving as a window. In a manner known per se e.g. an approach switch or other suitable detection-instrument triggers in response to the arrival at the correct position of a lid 4 the stroboscope lamp 1 that emits a flash in response thereon. This flash takes care of the described illumination of lid 4 and the forming of the video-picture of the lid 4.

In FIG. 2 some light beams are shown for explanation, in a strongly schematized fashion. The light beam indicated with 15 is directly emitted by lamp 1. The beam indicated with 16 comes from cylindrical mirror 7. The reflection beams 17 indicated with interrupted lines are within the viewing angle of the video-camera 6, whilst the diverging beam 18 is outside that angle. It should, therefore, be understood that camera 6 is optically adjusted such that it is able to see a full picture of the lid 4 via the half-transparent mirror 2. Therefore, the reflected beam 18 is outside the field of view of the camera.

I claim:

1. A method for inspecting the gutter of a container lid, comprising the steps of:
   placing the container lid in a path of a light,
   directing the light toward the gutter of the container lid, such that at least some light is reflected from the gutter, thereby forming an image of the gutter;
   monitoring the image formed by the reflected light;
   comparing the image of the gutter with a reference to determine if the gutter is flawed; and
   generating a rejection signal if the gutter is flawed.

2. The method of claim 1 wherein the light is directed toward the gutter from at least two directions.

3. The method of claim 2 wherein the container lid is positioned substantially in a plane and wherein the light is aimed toward the gutter from a first direction which defines an angle with the plane of between about 45 degrees and about 90 degrees and from a second direction which defines an angle with the plane of between about 90 degrees and about 135 degrees.

4. An apparatus for inspecting the gutter of a container lid, comprising:
   a light source;
   means for directing light emitted from the light source toward the gutter of the container lid, such that at least some of the light is reflected from the gutter to form an image of the gutter, said directing means positioned between the light source and the container lid;
   means for monitoring the image formed by the reflected light;
   means for storing a reference picture;
   means for comparing the image of the gutter with the reference picture to determine if the gutter is flawed; and
   means for generating a rejection signal if the gutter is flawed.

5. The apparatus of claim 4 wherein the means for directing light from the light source toward the gutter of the container lid comprises a mirror positioned between the light source and the container lid.

6. The apparatus of claim 5 wherein the mirror is substantially cylindrical.

7. The apparatus of claim 5 wherein the light source comprises means for generating a diverging beam which approaches the gutter of the container lid via the mirror and means for generating a converging beam which approaches the gutter of the container lid directly.

8. The apparatus of claim 4 wherein the monitoring means comprises a video camera and a mirror positioned in the path of the reflected light for directing the image formed by the reflected light into the video camera.

9. The apparatus of claim 8 wherein the mirror is semi-transparent and is positioned between the light source and the lid, such that light passing from the light source to the gutter of the lid is transmitted through the mirror and light reflected from the lid is reflected by the mirror into the video camera.

* * * * *